United States Patent
Edgell et al.

(10) Patent No.: US 8,942,807 B2
(45) Date of Patent: Jan. 27, 2015

(54) HEADER ASSEMBLIES FOR IMPLANTABLE MEDICAL DEVICES

(75) Inventors: John M. Edgell, Plymouth, MN (US); Lawrence D. Swanson, White Bear Lake, MN (US); Nick A. Youker, River Falls, WI (US)

(73) Assignee: Cardiac Pacemakers, Inc., St. Paul, MN (US)

(*) Notice: Subject to any disclaimer, the term of this patent is extended or adjusted under 35 U.S.C. 154(b) by 520 days.

(21) Appl. No.: 12/813,042

(22) Filed: Jun. 10, 2010

(65) Prior Publication Data

US 2010/0318156 A1 Dec. 16, 2010

Related U.S. Application Data

(60) Provisional application No. 61/185,786, filed on Jun. 10, 2009.

(51) Int. Cl.
*A61N 1/375* (2006.01)

(52) U.S. Cl.
CPC .................................. *A61N 1/3752* (2013.01)
USPC ........................................................ 607/37

(58) Field of Classification Search
CPC .... A61N 1/375; A61N 1/3752; A61N 1/3754
USPC ..................................................... 607/36–38
See application file for complete search history.

(56) References Cited

U.S. PATENT DOCUMENTS

| | | | |
|---|---|---|---|
| 5,620,477 A * | 4/1997 | Pless et al. | 607/37 |
| 5,626,626 A | 5/1997 | Carson | |
| 5,683,433 A | 11/1997 | Carson | |
| 5,843,141 A | 12/1998 | Bischoff et al. | |
| 6,062,915 A | 5/2000 | Costello et al. | |
| 6,080,188 A | 6/2000 | Rowley et al. | |
| 6,112,121 A * | 8/2000 | Paul et al. | 607/37 |
| 6,606,521 B2 | 8/2003 | Paspa et al. | |
| 6,921,295 B2 | 7/2005 | Sommer et al. | |
| 7,155,283 B2 | 12/2006 | Ries et al. | |
| 2006/0259092 A1 | 11/2006 | Spadgenske et al. | |

* cited by examiner

*Primary Examiner* — Kennedy Schaetzle
*Assistant Examiner* — Erica Lee
(74) *Attorney, Agent, or Firm* — Pauly, Devries Smith & Deffner, LLC

(57) ABSTRACT

Embodiments of the invention are related to header assemblies for implantable medical devices, amongst other things. In an embodiment the invention includes a medical device including a header assembly housing. The header assembly housing can include a dielectric material, the header assembly housing can define a port aperture for receiving a connector pin of a stimulation lead. The port aperture can have a first end and a second end and a reflective insert disposed within the header assembly housing proximate to the second end. The reflective insert can be configured to enhance the view of the second end from outside of the header assembly housing. Other embodiments are also included herein.

13 Claims, 10 Drawing Sheets

HEADER ASSEMBLIES FOR IMPLANTABLE MEDICAL DEVICES

This application claims the benefit of U.S. Provisional Application No. 61/185,786 filed Jun. 10, 2009, the contents of which are herein incorporated by reference.

TECHNICAL FIELD

This disclosure relates generally to implantable medical devices, and more particularly, to header assemblies for implantable medical devices, amongst other things.

BACKGROUND OF THE INVENTION

Implantable medical devices (IMDs) are commonly used to provide treatment to patients. Implantable medical devices can include cardiac rhythm management devices and neurological stimulation devices, amongst others. Some types of implantable medical devices deliver electrical stimuli to a target tissue via a lead wire ("stimulation lead") or catheter having one or more electrodes disposed in or about the target tissue. The stimulation lead is frequently connected to a pulse generator housing via a structure commonly referred to as a header assembly. The header assembly serves to provide fixation of the proximal end of the stimulation lead and electrically couples the stimulation lead with the pulse generator.

During the procedure of implanting the implantable medical system, the stimulation leads are generally threaded through a major vein (typically the subclavian vein) in the upper chest and into the heart with the help of imaging devices. The distal ends of the stimulation leads include electrodes and transvenously pass to the heart. Once the stimulation leads are in the proper position, they are attached to the pulse generator via the header assembly. Specifically, the proximal ends of the stimulation leads are inserted into ports in the header assembly and then secured in place, typically with a set screw.

SUMMARY OF THE INVENTION

Embodiments of the invention are related to header assemblies for implantable medical devices, amongst other things. In an embodiment the invention includes a medical device including a header assembly housing. The header assembly housing can include a dielectric material, the header assembly housing can define a port aperture for receiving a connector pin of a stimulation lead. The port aperture can have a first end and a second end and a reflective insert disposed within the header assembly housing proximate to the second end. The reflective insert can be configured to enhance the view of the second end from outside of the header assembly housing.

In an embodiment, the invention includes a medical device including a header assembly housing comprising a non-translucent dielectric material, the header assembly defining a port aperture for receiving a connector pin of a stimulation lead, the port aperture comprising an open first end and a closed second end. The medical device can also include a translucent window block disposed within the header assembly housing, the translucent window block configured to allow a view of the closed second end of the port aperture from outside of the header assembly housing.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope of the present invention is defined by the appended claims and their legal equivalents.

BRIEF DESCRIPTION OF THE DRAWINGS

The invention may be more completely understood in connection with the following drawings, in which.

While the invention is susceptible to various modifications and alternative forms, specifics thereof have been shown by way of example and drawings, and will be described in detail. It should be understood, however, that the invention is not limited to the particular embodiments described. On the contrary, the intention is to cover modifications, equivalents, and alternatives falling within the spirit and scope of the invention.

DETAILED DESCRIPTION OF THE INVENTION

During the procedure of implanting a medical device, such as a pacemaker or an implantable cardioverter-defibrillator, stimulation leads are generally introduced through a major vein in the upper chest and into the heart. Once the leads are in the proper position, they are attached to the pulse generator via the header assembly. Specifically, the proximal ends of the stimulation leads are inserted into ports in the header and then secured in place. However, it can be difficult to ensure that the proximal end of the stimulation lead is fully inserted into the corresponding port in the header. If the proximal end of the stimulation lead is not fully inserted, electrical contact may not be achieved and the stimulation lead may be inoperative.

Embodiments herein can include systems and devices for facilitating proper insertion of stimulation leads into the ports of a header assembly. In an embodiment, connector blocks within the header assembly are treated so that they exhibit a color that is in contrast with the color of the connector pin on the stimulation lead. In this manner a user implanting the system, such as a physician, can more clearly see when the connector pin has passed through the connector block, indicating that the stimulation lead has been fully inserted.

In another embodiment, a reflective insert is put into the header assembly in order to enhance the view that a user has when inserting the proximal end of a stimulation lead into the corresponding port in the header. Various aspects of exemplary embodiments will now be described in greater detail.

Figure 1:
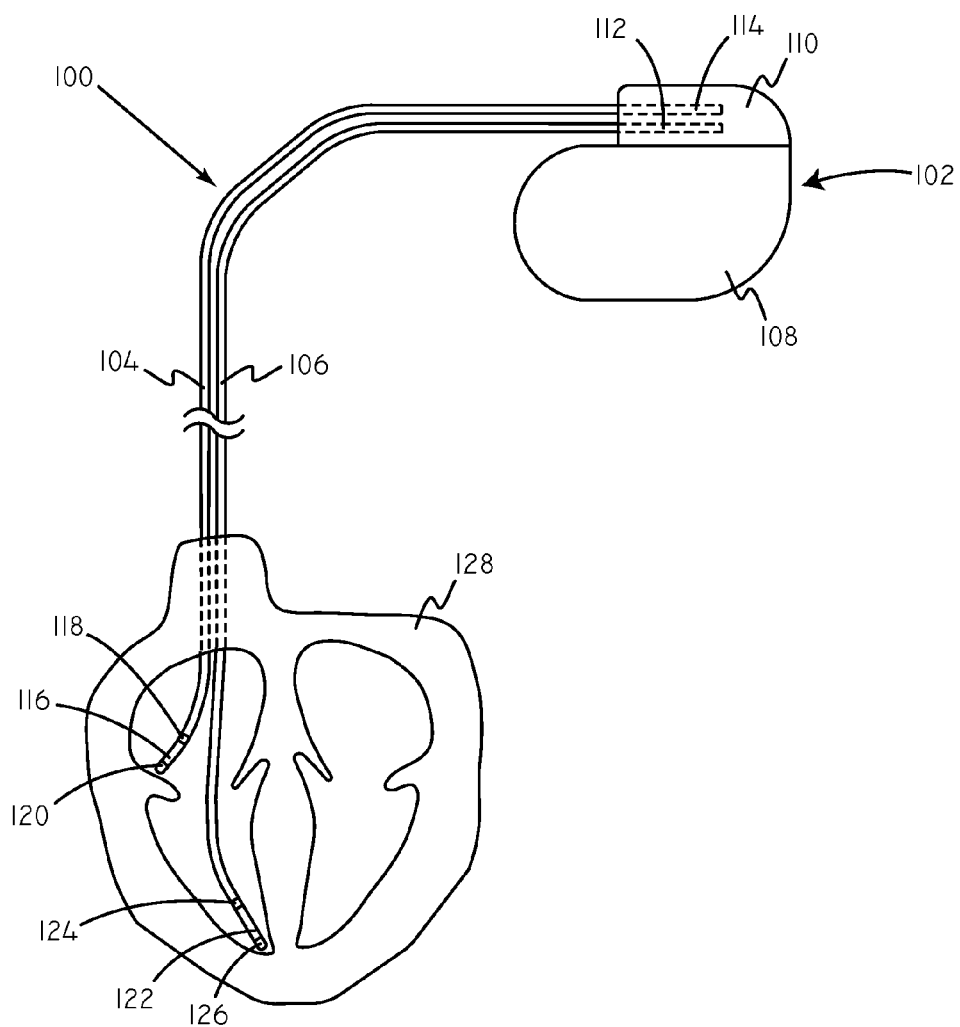
FIG. 1 is a schematic view of an implantable medical device system in accordance with an embodiment.

FIG. 1 is a schematic view of an implantable medical system 100 shown in conjunction with a heart 128. Electrical stimulation leads 104, 106 electrically couple a pulse generator 102 with the heart 128. Distal ends 116, 122 of the electrical stimulation leads 104, 106 have one or more electrodes 118, 120, 124, 126, which are disposed within the heart 128. Connector pins (not shown in this view) on the proximal ends of the electrical stimulation leads 104, 106 are disposed within port apertures 112, 114 defined by the header assembly 110. During implantation, the connector pins on the proximal ends of the leads 104, 106 are inserted into port apertures 112, 114 and into connector blocks (not shown in this view) and then secured in place, such as with a set screw.

The header assembly 110 is electrically coupled to the pulse generator housing 108. Typically, wires made from a conductive material pass from the pulse generator housing 108 to the connector blocks within the header assembly.

In operation, the pulse generator 102 may generate pacing pulses and/or therapeutic shocks which are delivered through the header assembly 110, through the leads 104, 106, and to the heart 128. In many embodiments, the leads 104, 106 include a material that is electrically conductive in order to deliver the pacing pulses or therapeutic shocks.

Figure 2:
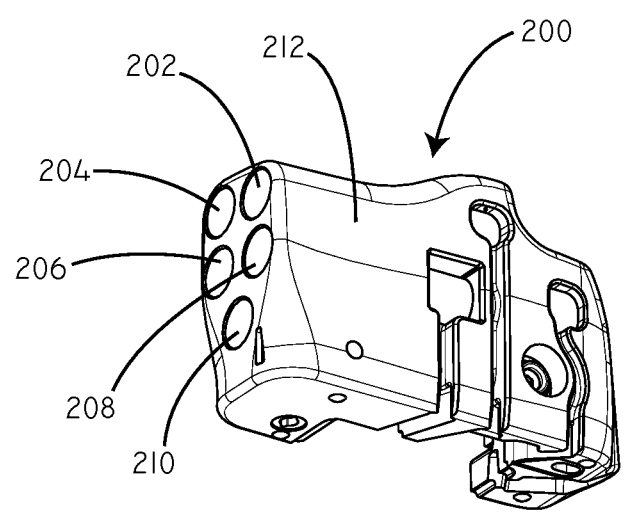
FIG. 2 is a schematic view of a header assembly in accordance with an embodiment.

FIG. 2 is a schematic view of a header assembly 200 in accordance with an embodiment. The header assembly 200 provides fixation of the proximal ends of the stimulation leads and facilitates electrical communication between electrical components within the pulse generator housing and the electrical stimulation leads in the heart. The header assembly 200 includes a header assembly housing 212 that defines multiple port apertures 202, 204, 206, 208, 210 that are configured to receive a connector pin of an electrical stimulation lead. Though there are five port apertures depicted in FIG. 2, it will be appreciated that embodiments within the scope herein can include a greater or less number of port apertures. For example, in some embodiments the header assembly can include between one and twenty port apertures. In some embodiments, a single port aperture can include a plurality of connection electrodes, such as connector blocks, arranged serially.

The port apertures 202, 204, 206, 208, 210 have a first end and a second end. When connecting a stimulation lead to the header assembly, the tip of a connector pin of an electrical stimulation lead enters the first end of the port aperture and progresses to the second end of the port aperture.

The header assembly housing 212 can be made of a dielectric material (electrical insulator). Exemplary dielectric materials can include various polymers and glasses, amongst others. A specific example is TECOTHANE® brand polyurethane polymer, commercially available from Lubrizol Advanced Materials, Inc., Wilmington, Mass.

The header housing 212 can be formed through a molding process. However, it will be appreciated that the header housing 212 can also be formed in other ways. In multiple embodiments the header housing is at least partially translucent such that the location of the connector pin of an electrical stimulation lead can be viewed. Such embodiments allow visualization of insertion of the connector pin of an electrical stimulation lead into the header assembly housing. In some embodiments, the header assembly housing is completely translucent.

Figure 3:
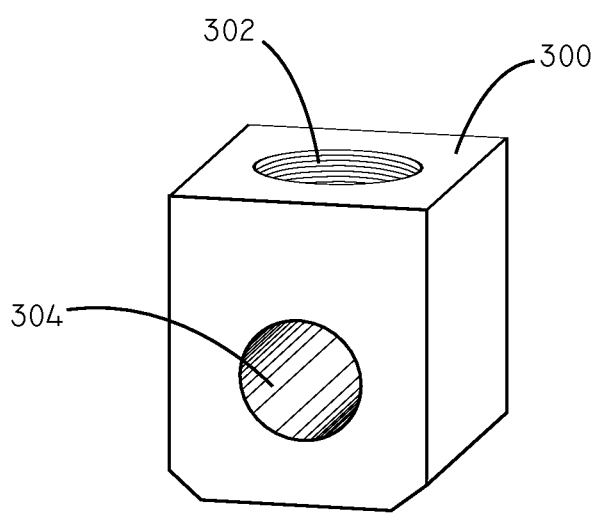
FIG. 3 is a schematic view of a connector block in accordance with an embodiment.

FIG. 3 is a schematic view of a connector block in accordance with an embodiment. The connector block 300 defines a pin aperture 304 that is configured to receive a connector pin of an electrical stimulation lead and a threaded aperture that is configured to receive a fastener, such as a screw for example. As mentioned above, the connector block 300 serves to provide fixation of the proximal end of a stimulation lead and electrically couples the stimulation leads with the pulse generator.

The pin aperture 304 defined by the connector block 300 is configured to at least partially align with the port aperture defined by the header assembly such that the connector pin of the stimulation lead passes through the first end of the port aperture of the header assembly, through the connector block, and to the second end of the port aperture of the header assembly.

The connector block 300 can be constructed of a conductive material such as copper, stainless steel, titanium, silver, or the like. The connector block 300 can be machined, die cast, molded, or the like. The connector block 300 is generally disposed within the header assembly. The connector block 300 can be configured to be visually distinct from the connector pin of an electrical stimulation lead. For example, in multiple embodiments, the connector block 300 is a color that is distinct from the color of the connector pin of an electrical stimulation lead. Such a result can be achieved through applying a color to the connector block. In various embodiments, a color can be applied to the connector block by depositing a layer of a material having a particular color on the connector block.

In one embodiment, a layer of a material can be applied to the connector block 300 via physical vapor deposition process. In another embodiment, the connector block 300 can be anodized to deposit a metal oxide layer. In various embodiments, a layer of a paint or dye can be applied to the connector block 300. Other methods to produce connector block 300 that is visually distinct as compared to a connector pin can also be used and are within the scope of the technology disclosed herein.

The connector block can then be inserted in the header assembly housing (see FIG. 2) for use. In some embodiments, the connector block is inserted into the header assembly housing through an insert molding process.

Figure 4:
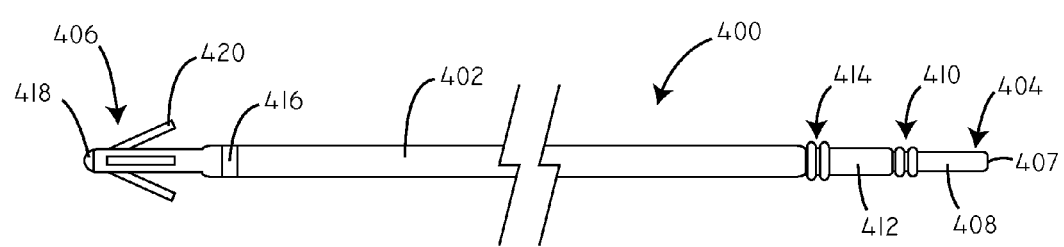
FIG. 4 is a schematic view of a stimulation lead in accordance with an embodiment.

FIG. 4 is a schematic view of a stimulation lead in accordance with an embodiment. The stimulation lead 400 has a stimulation lead body 402 where the distal end 406 has a tip electrode 418, a passive fixation element 420, and a ring electrode 416. In some embodiments, the fixation element 420 may be omitted. In various embodiments, the stimulation lead 400 may include more than two electrodes or less than two electrodes.

The proximal end 404 of the stimulation lead includes a connector pin 408. The connector pin 408 can include a proximal tip 407. The proximal end 404 of the stimulation lead can also include a first sealing ring 410 and a second sealing ring 414 disposed thereon. The connector pin 408 can serve as an electrical contact. The stimulation lead can also include a second electrical contact 412 near the proximal end 404 of the lead. In various embodiments, the stimulation lead can include between about one and twenty electrical contacts near the proximal end 404 of the lead.

As described in FIG. 1, the stimulation lead 400 is configured to convey electrical stimulation pulses from the pulse generator to the heart. For this reason, the stimulation lead includes an electrically conductive material (not shown) along the length of the stimulation lead 400. The body of the stimulation lead 402 can further include one or more electrically insulating materials to sufficiently insulate the electrically conductive material within the stimulation lead 400.

Figure 5:
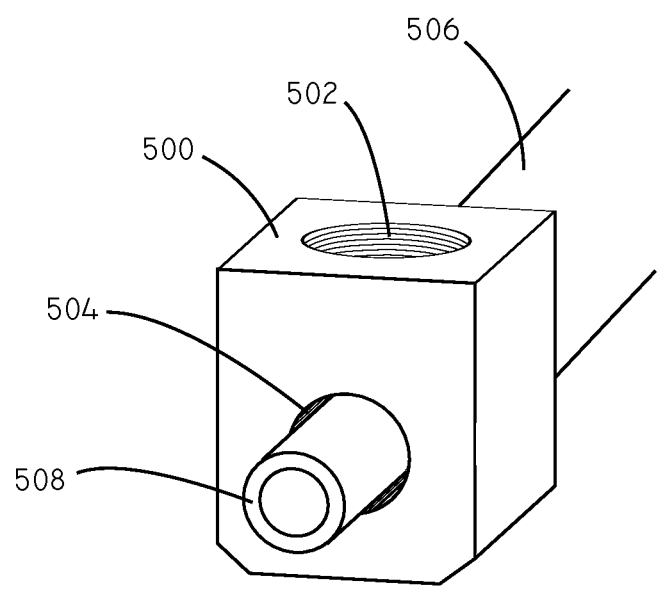
FIG. 5 is a schematic view of a stimulation lead interfacing with a connector block in accordance with an embodiment.

FIG. 5 is a schematic view of a stimulation lead 506 interfacing with a connector block 500 in accordance with an embodiment. A connector pin 508 on the proximal end of the stimulation lead 506 is shown disposed within a pin aperture 504 defined by the connector block 500. A threaded aperture 502 defined by the connector block 500 is configured to receive a fastener, such as a set screw, that can secure the connector pin 508 within the pin aperture 504 of the connector block 500.

As discussed above with regard to FIG. 3, the connector block 500 can be configured to be visually distinct from the connector pin 508, such as through having a distinct color from the connector pin 508. With distinct colors, it can be easy to visually inspect the header assembly and determine whether the proximal end of the stimulation lead is properly inserted into the port aperture of the header assembly. For example, it can be relatively easy to identify that the connector pin of a stimulation lead has passed through the connector block when there is a visual contrast between the connector pin and the connector block.

Figure 6:
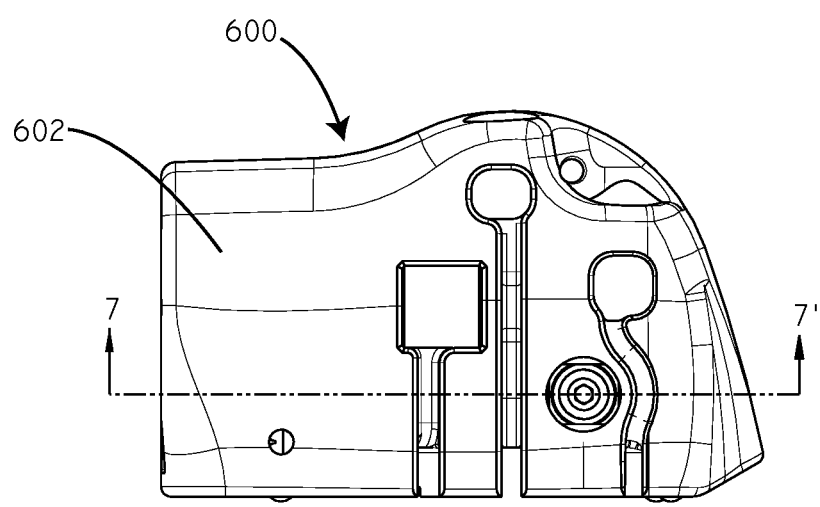
FIG. 6 is a schematic side view of a header assembly in accordance with an embodiment.
Figure 7:
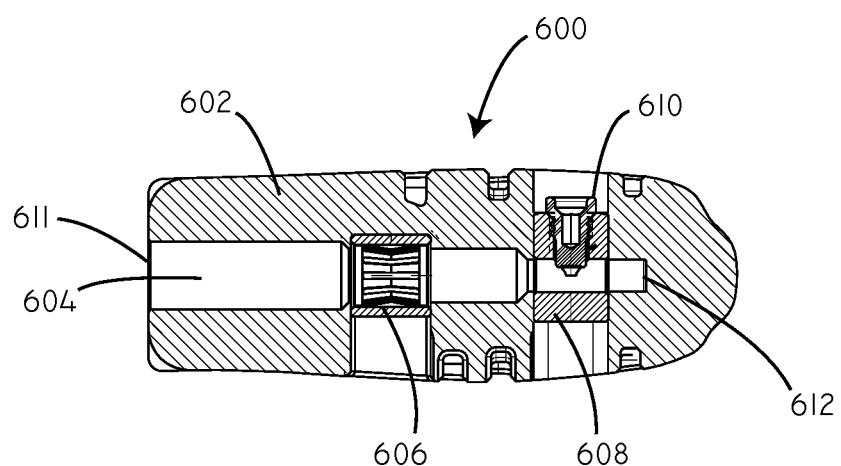
FIG. 7 is a schematic cross-sectional view of a header assembly as taken along line 7-7' of FIG. 6.

FIG. 6 is a schematic side view of a header assembly 600 in accordance with an embodiment. The header assembly 600 includes a header assembly housing 602. FIG. 7 is a schematic cross-sectional view of the header assembly 600 as taken along line 7-7' of FIG. 6. The header assembly 600 includes a header assembly housing 602 defining a port aperture 604 to receive a connector pin. The port aperture 604 includes a first end 611 and a second end 612. The second end 612 of the port aperture 604 can be configured to accommodate the proximal-most tip of a connector pin.

A first connector block 606 and a second connector block 608 are disposed within the header assembly 600, each defining apertures at least partially aligned with the port aperture 604 of the header body 602. Though two connector blocks are shown in FIG. 7 associated with a single port aperture, it will be appreciated that embodiments herein can include a different number of connector blocks. For example, in some embodiments, between one and ten connector blocks can be associated with a single port aperture. Electrical contacts on the stimulation lead can align with the first connector block 606 and the second connector block 608. A connector pin can fit within the second connector block 608 and can be secured in place with a set screw 610, which can also ensure proper electrical communication between the connector pin and the second connector block 608. In this embodiment, the first connector block 606 can include a compression type mechanism in order to provide electrical communication between the first connector block 606 and an electrical contact on the stimulation lead.

In some embodiments, a reflective insert can be disposed within the header assembly to make it easier to visualize when the stimulation lead is properly inserted into the header assembly. For example, the reflective insert can function to enhance the view of the area immediately adjacent to the connector block so it can be determined when the connector pin of the stimulation lead has properly passed through the connector block of the header assembly.

Figure 8:
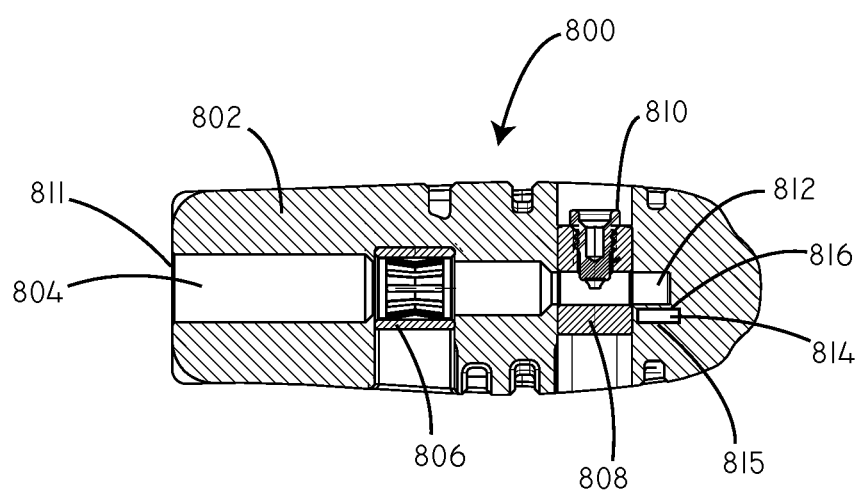
FIG. 8 is a schematic cross-sectional view of a header assembly in accordance with another embodiment.

FIG. 8 is a schematic cross-sectional view of a header assembly 800 in accordance with another embodiment. A header assembly housing 802 defines a port aperture 804 having a first end 811 and a second end 812. A first connector block 806 and second connector block 808 are disposed within the header assembly 800. A fastener, such as a screw 810, can be disposed within the second connector block 808 and can be configured to engage a connector pin of a stimulation lead.

A reflective insert 814 can be disposed within the header housing 802 proximate to the second end 812 of the port aperture 804. The reflective insert 814 can be configured to enhance the view of the second end 812 from outside of the header assembly 800. In various embodiments the reflective insert 814 exhibits substantially specular reflection. In some embodiments, the reflective insert 814 can include a first side 816 that is reflective and a second side 815 that is non-reflective. Reflected light from the reflective insert can facilitate visual inspection to determine whether or not the connector pin is properly positioned within a connector block.

It will be appreciated that many different materials can be used to form the reflective insert. For example, the reflective insert can include, but is not limited to, polymers, metals, ceramics, and the like. In some embodiments the reflective insert can include a base material with a reflective coating disposed on one or both sides of the reflective insert.

It will be appreciated that reflective inserts can take on various shapes. In some embodiments, the reflective insert can be substantially flat. In other embodiments, the reflective insert can be curved. In some embodiments, the reflective insert can be parabolic. In some embodiments, the reflective insert can be made from a sheet of material that is either flat or curved. In some embodiments, the reflective insert can be made from a block of material with either a flat or curved surface.

Figure 9:
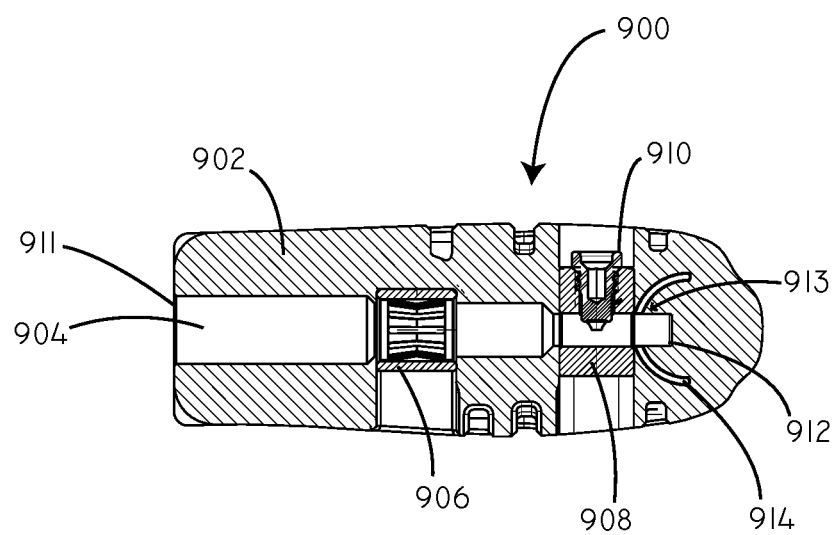
FIG. 9 is a schematic cross-sectional view of a header assembly in accordance with another embodiment.

Referring now to FIG. 9, a schematic cross-sectional view is shown of a header assembly 900 in accordance with an embodiment. The header assembly 900 includes a header assembly housing 902. The header assembly housing 902 defines a port aperture 904. The port aperture 904 includes an open first end 911 and a closed second end 912. A first connector block 906 and a second connector block 908 are disposed within the header assembly housing 902. A fastening device 910, such as a set screw, can be included within the header assembly housing 902. A reflective insert 914 can be disposed within the header assembly housing 902. Reflective insert 914 can be positioned adjacent to the second connector block 908, in order to enhance the view of the second end 912 of the port aperture 904. In this manner, when a connector pin of a stimulation lead is inserted through the second connector block 908 extending to the second end 912 of the port aperture 904, the view of the connector pin will be enhanced by the reflective insert 914. Reflective insert 914 can be parabolic in shape and can define a central aperture 913.

Figure 10:
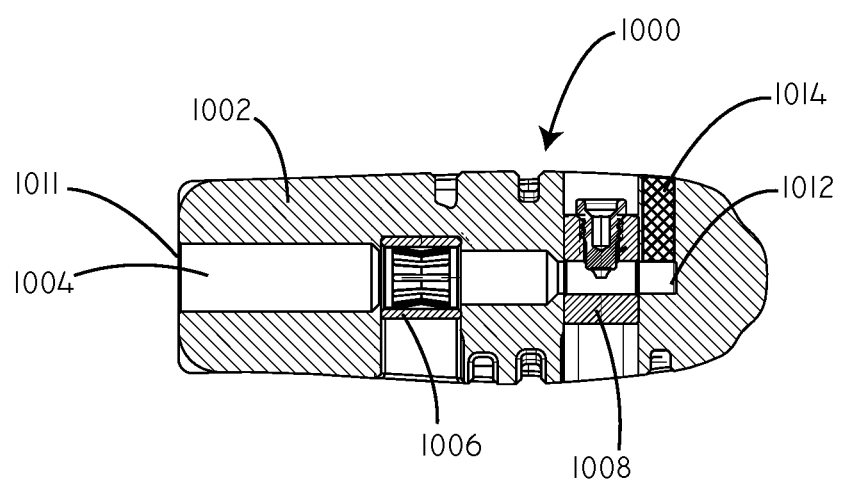
FIG. 10 is a schematic cross-sectional view of a header assembly in accordance with another embodiment.

In some embodiments, the view of the second end of the port aperture can effectively be enhanced by making only specific portions of the header assembly housing translucent. For example, the header assembly housing can be constructed so that most portions of it are opaque (non-translucent), and only a specific "window" portion is translucent. Referring now to FIG. 10, a schematic cross-sectional view is shown of a header assembly 1000 in accordance with an embodiment. The header assembly 1000 includes a header assembly housing 1002. The header assembly housing 1002 defines a port aperture 1004. The port aperture 1004 includes a first end 1011 and a second end 1012. A first connector block 1006 and a second connector block 1008 are disposed within the header assembly housing 1002.

The header assembly housing 1002 can be opaque, except for a translucent window block 1014 (or window plug). The header assembly housing 1002 can be constructed of a polymer or a similar material. The translucent window block 1014 can be constructed of a translucent polymer or glass, though other materials can also be used. The translucent window block 1014 can take on various shapes. By way of example, the translucent window block 1014 can be cylindrical, conical, frusto-conical, polyhedral, or the like. In some embodiments, the translucent window block 1014 is configured to have no optical magnification properties. In other embodiments, the translucent window block 1014 can have optical magnification properties.

It should be noted that, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as "arranged", "arranged and configured", "constructed and arranged", "constructed", "manufactured and arranged", and the like.

One of ordinary skill in the art will understand that the modules, circuitry, and methods shown and described herein with regard to various embodiments of the invention can be implemented using software, hardware, and combinations of software and hardware. As such, the illustrated and/or described modules and circuitry are intended to encompass software implementations, hardware implementations, and software and hardware implementations.

All publications and patent applications in this specification are indicative of the level of ordinary skill in the art to which this invention pertains. All publications and patent applications are herein incorporated by reference to the same extent as if each individual publication or patent application was specifically and individually indicated by reference.

This application is intended to cover adaptations or variations of the present subject matter. It is to be understood that the above description is intended to be illustrative, and not restrictive. The scope of the present subject matter should be determined with reference to the appended claims, along with the full scope of equivalents to which such claims are entitled.

What is claimed is:

1. A medical device comprising:
   a header assembly housing comprising a translucent dielectric material, the header assembly defining a port aperture comprising an open first end and a closed second end and configured for receiving a connector pin of an electrical stimulation lead;
   a connector block comprising a conductive material, the connector block disposed within the header assembly housing and defining a pin aperture aligned with the port aperture defined by the header assembly, the pin aperture configured to receive the connector pin of the electrical stimulation lead; and
   a reflective insert disposed within the header assembly housing adjacent to the connector block and external to the port aperture, the reflective insert configured to enhance a view of the closed second end of the port aperture from outside of the header assembly housing, the reflective insert exhibiting substantially specular reflection.

2. The medical device of claim 1, the reflective insert comprising a reflective surface and a non-reflective surface.

3. The medical device of claim 1, the reflective insert comprising a sheet of material.

4. The medical device of claim 1, the reflective insert comprising a base material with a reflective coating disposed thereon.

5. The medical device of claim 1, the reflective insert comprising a parabolic shape.

6. The medical device of claim 1, the reflective insert defining a central aperture.

7. The medical device of claim 1, the dielectric material comprising a translucent polymer.

8. The medical device of claim 1, the header assembly housing coupled to a pulse generator housing.

9. The medical device of claim 1, the reflective insert comprising a material selected from the group consisting of polymers, metals, and ceramics.

10. A medical device comprising:
    a header assembly housing comprising a translucent dielectric material, the header assembly defining a port aperture having an open first end and a closed second end and configured for receiving a connector pin of an electrical stimulation lead;
    a connector block comprising a conductive material, the connector block disposed within the header assembly housing and defining a pin aperture aligned with the port aperture defined by the header assembly, the pin aperture configured to receive the connector pin of the electrical stimulation lead; and
    a reflective insert disposed within the header assembly housing adjacent to the connector block, the reflective insert configured to enhance a view of the closed second end of the port aperture from outside of the header assembly housing, wherein the reflective insert is offset from a center axis of the port aperture, the reflective insert exhibiting substantially specular reflection.

11. The medical device of claim 10, the reflective insert comprising a parabolic shape.

12. The medical device of claim 11, the parabolic shape being normal to the center axis of the port aperture.

13. A medical device comprising:
    a header assembly housing comprising a translucent dielectric material, the header assembly defining a port aperture comprising an open first end and a closed second end and configured for receiving a connector pin of an electrical stimulation lead;
    a connector block comprising a conductive material, the connector block disposed within the header assembly housing and defining a pin aperture aligned with the port aperture defined by the header assembly, the pin aperture configured to receive the connector pin of the electrical stimulation lead; and
    a reflective insert disposed within the header assembly housing adjacent to the connector block and external to the port aperture, the reflective insert configured to enhance a view of the closed second end of the port aperture from outside of the header assembly housing, the reflective insert comprising a parabolic shape.

* * * * *